(12) United States Patent
Sorensen et al.

(10) Patent No.: US 9,861,522 B2
(45) Date of Patent: Jan. 9, 2018

(54) PHACOEMULSIFICATION HAND PIECE WITH INTEGRATED ASPIRATION PUMP

(75) Inventors: Gary Sorensen, Laguna Niguel, CA (US); Glenn Sussman, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 62 days.

(21) Appl. No.: 13/325,549

(22) Filed: Dec. 14, 2011

(65) Prior Publication Data

US 2012/0083728 A1  Apr. 5, 2012

Related U.S. Application Data

(63) Continuation of application No. 12/633,363, filed on Dec. 8, 2009.

(51) Int. Cl.
*A61F 9/00* (2006.01)
*A61F 9/007* (2006.01)
*A61M 5/142* (2006.01)

(52) U.S. Cl.
CPC ..... *A61F 9/00745* (2013.01); *A61M 5/14228* (2013.01)

(58) Field of Classification Search
CPC ...... A61F 9/00745; A61F 9/007; F04B 43/12; F04B 43/08261; A61M 5/14228
USPC ..... 604/22, 289, 294, 297, 298, 300, 48, 65, 604/67
See application file for complete search history.

(56) References Cited

U.S. PATENT DOCUMENTS

| | | | |
|---|---|---|---|
| 1,061,142 A | 5/1913 | Nikola | |
| 1,061,206 A | 5/1913 | Nikola | |
| 1,874,667 A * | 8/1932 | Wada | A61M 1/1037 222/209 |
| 2,015,123 A * | 9/1935 | Pennell | F04B 43/12 417/477.4 |
| 2,987,004 A | 6/1961 | Murray | |
| 3,447,478 A * | 6/1969 | Anton | F04B 43/1253 417/477.8 |
| 3,487,784 A | 1/1970 | Rafferty et al. | |
| 3,589,363 A * | 6/1971 | Banko | A61B 17/320068 604/22 |
| 3,724,974 A | 4/1973 | Molimard | |

(Continued)

FOREIGN PATENT DOCUMENTS

| | | |
|---|---|---|
| CA | 2316640 | 2/2001 |
| CA | 2649867 A1 | 6/2001 |

(Continued)

OTHER PUBLICATIONS

International Search Report for PCT/US2010/058931, filed Dec. 3, 2010, Publication No. 2011071775, Published Jun. 16, 2011, 2 pages.

(Continued)

*Primary Examiner* — Kevin C Sirmons
*Assistant Examiner* — William Carpenter (57) ABSTRACT

An ophthalmic surgical hand piece comprises a driver coupled to a horn. The horn is coupled to a needle. An aspiration pump is integral with the hand piece and is located close to the needle. A rigid length of aspiration line is located between the aspiration pump and the needle. An optional pressure sensor is located between the aspiration pump and the needle as well.

8 Claims, 5 Drawing Sheets

(56) References Cited

U.S. PATENT DOCUMENTS

| | | |
|---|---|---|
| 3,784,323 A | 1/1974 | Sausse |
| 3,996,935 A * | 12/1976 | Banko .................. 604/22 |
| 4,140,118 A | 2/1979 | Jassawalla |
| 4,187,057 A | 2/1980 | Xanthopoulos |
| 4,205,948 A | 6/1980 | Jones |
| 4,255,081 A | 3/1981 | Oklejas et al. |
| 4,320,761 A * | 3/1982 | Haddad ............ A61F 9/00763 |
| | | 408/58 |
| 4,392,794 A | 7/1983 | Foxcroft |
| 4,405,289 A | 9/1983 | Nakashima |
| 4,479,761 A | 10/1984 | Bilstad et al. |
| 4,493,706 A | 1/1985 | Borsanyi et al. |
| 4,530,647 A | 7/1985 | Uno |
| 4,537,561 A | 8/1985 | Xanthopoulos |
| 4,657,490 A | 4/1987 | Abbott |
| 4,661,093 A | 4/1987 | Beck et al. |
| 4,684,328 A | 8/1987 | Murphy |
| 4,705,500 A | 11/1987 | Reimels et al. |
| 4,713,051 A | 12/1987 | Steppe et al. |
| 4,758,238 A | 7/1988 | Sundblom et al. |
| 4,764,165 A | 8/1988 | Reimels et al. |
| 4,768,547 A | 9/1988 | Danby et al. |
| 4,790,726 A | 12/1988 | Balkau et al. |
| 4,798,580 A | 1/1989 | Demeo et al. |
| 4,838,865 A | 6/1989 | Flank et al. |
| 4,854,825 A | 8/1989 | Bez et al. |
| 4,861,332 A | 8/1989 | Parisi |
| 4,909,710 A | 3/1990 | Kaplan et al. |
| 4,909,713 A | 3/1990 | Finsterwald et al. |
| 4,921,477 A | 5/1990 | Davis |
| 4,923,375 A | 5/1990 | Ejlersen |
| 4,935,005 A | 6/1990 | Haines |
| 4,963,131 A | 10/1990 | Wortrich |
| 5,038,965 A | 8/1991 | Cater |
| 5,041,096 A | 8/1991 | Beuchat et al. |
| 5,044,902 A * | 9/1991 | Malbec ................ F04B 43/12 |
| | | 417/477.2 |
| 5,046,486 A | 9/1991 | Grulke et al. |
| 5,106,366 A | 4/1992 | Steppe |
| 5,185,002 A | 2/1993 | Venturini |
| 5,195,960 A | 3/1993 | Hossin et al. |
| 5,207,647 A | 5/1993 | Phelps |
| 5,257,917 A | 11/1993 | Minarik |
| 5,263,830 A | 11/1993 | Goi et al. |
| 5,267,956 A | 12/1993 | Beuchat |
| 5,273,517 A | 12/1993 | Barone et al. |
| 5,302,093 A | 4/1994 | Owens et al. |
| 5,316,440 A | 5/1994 | Kijima et al. |
| 5,342,181 A | 8/1994 | Schock et al. |
| 5,350,357 A | 9/1994 | Kamen et al. |
| 5,364,342 A | 11/1994 | Beuchat et al. |
| 5,392,653 A | 2/1995 | Zanger et al. |
| 5,403,277 A | 4/1995 | Dodge et al. |
| 5,429,485 A | 7/1995 | Dodge |
| 5,429,602 A | 7/1995 | Hauser |
| 5,443,370 A | 8/1995 | Wang |
| 5,460,490 A | 10/1995 | Carr et al. |
| 5,462,416 A | 10/1995 | Dennehey et al. |
| 5,470,312 A | 11/1995 | Zanger et al. |
| 5,484,239 A | 1/1996 | Chapman et al. |
| 5,487,747 A | 1/1996 | Stagmann et al. |
| 5,518,378 A | 5/1996 | Neftel et al. |
| 5,533,976 A | 7/1996 | Zaleski et al. |
| 5,542,918 A | 8/1996 | Atkinson |
| 5,554,013 A | 9/1996 | Owens et al. |
| 5,575,632 A | 11/1996 | Morris et al. |
| 5,588,815 A | 12/1996 | Zaleski et al. |
| 5,630,711 A | 5/1997 | Luedtke et al. |
| 5,688,112 A | 11/1997 | Garay |
| 5,697,910 A | 12/1997 | Cole et al. |
| 5,705,018 A | 1/1998 | Hartley |
| 5,709,539 A | 1/1998 | Hammer et al. |
| 5,733,256 A | 3/1998 | Costin |
| 5,746,708 A | 5/1998 | Giesler et al. |
| 5,746,719 A | 5/1998 | Farra et al. |
| 5,759,017 A | 6/1998 | Patton et al. |
| 5,788,667 A | 8/1998 | Stoller |
| 5,810,765 A | 9/1998 | Oda |
| 5,853,386 A | 12/1998 | Davis et al. |
| 5,879,363 A * | 3/1999 | Urich .................. 606/167 |
| 5,897,524 A | 4/1999 | Wortrich et al. |
| 5,906,598 A | 5/1999 | Giesler et al. |
| 5,910,110 A | 6/1999 | Bastable |
| 5,927,956 A | 7/1999 | Lim et al. |
| 5,951,581 A * | 9/1999 | Saadat et al. ............ 606/170 |
| 5,957,914 A * | 9/1999 | Cook .................. A61B 18/26 |
| | | 606/10 |
| 5,972,012 A * | 10/1999 | Ream et al. ............ 606/170 |
| 5,996,634 A | 12/1999 | Dennehey et al. |
| 6,012,999 A | 1/2000 | Patterson |
| 6,058,779 A | 5/2000 | Cole |
| 6,059,544 A | 5/2000 | Jung et al. |
| 6,071,639 A * | 6/2000 | Bryant ................ H01M 2/1055 |
| | | 429/100 |
| 6,109,895 A | 8/2000 | Ray et al. |
| 6,117,149 A | 9/2000 | Sorensen et al. |
| 6,129,699 A | 10/2000 | Haight et al. |
| 6,217,543 B1 * | 4/2001 | Anis et al. .............. 604/22 |
| 6,241,700 B1 * | 6/2001 | Leukanech ............ 604/19 |
| 6,270,326 B1 * | 8/2001 | Kuriyama ............ A61M 5/14224 |
| | | 417/477.4 |
| 6,293,926 B1 | 9/2001 | Sorensen |
| 6,296,460 B1 | 10/2001 | Smith |
| 6,416,293 B1 | 7/2002 | Bouchard et al. |
| 6,491,661 B1 | 12/2002 | Boukhny et al. |
| 6,527,765 B2 * | 3/2003 | Kelman et al. .......... 606/22 |
| 6,551,080 B2 | 4/2003 | Andersen et al. |
| 6,572,349 B2 | 6/2003 | Sorensen et al. |
| 6,599,277 B2 | 7/2003 | Neubert |
| 6,655,934 B2 | 12/2003 | Mittelstein et al. |
| 6,689,146 B1 * | 2/2004 | Himes .................. 606/167 |
| 6,723,065 B2 | 4/2004 | Kishimoto |
| 6,749,403 B2 | 6/2004 | Bryant et al. |
| 6,811,386 B2 | 11/2004 | Hedington et al. |
| 6,814,547 B2 | 11/2004 | Childers et al. |
| 6,868,987 B2 | 3/2005 | Hedington |
| 6,958,058 B1 | 10/2005 | Hunter, Sr. et al. |
| 6,962,488 B2 | 11/2005 | Davis et al. |
| 7,063,688 B2 | 6/2006 | Say |
| 7,070,574 B2 * | 7/2006 | Jackson et al. ............ 604/35 |
| 7,144,383 B2 | 12/2006 | Arnett et al. |
| 7,150,607 B2 | 12/2006 | Pelmulder et al. |
| 7,238,164 B2 | 7/2007 | Childers et al. |
| 7,273,359 B2 | 9/2007 | Blight et al. |
| 7,393,189 B2 | 7/2008 | Davis et al. |
| 7,445,436 B2 | 11/2008 | Mittelstein et al. |
| 7,540,855 B2 | 6/2009 | Lumpkin et al. |
| 7,604,610 B2 | 10/2009 | Shener et al. |
| 7,632,080 B2 | 12/2009 | Tracey et al. |
| 7,645,127 B2 | 1/2010 | Hagen et al. |
| 7,695,242 B2 | 4/2010 | Fuller |
| 7,758,515 B2 | 7/2010 | Hibner |
| 7,775,780 B2 | 8/2010 | Hopkins et al. |
| 7,967,777 B2 | 6/2011 | Edwards et al. |
| 8,070,712 B2 | 12/2011 | Muri et al. |
| 8,087,909 B2 | 1/2012 | Shener |
| 8,162,633 B2 | 4/2012 | Edwards |
| 8,617,106 B2 * | 12/2013 | Zacharias ............ A61M 1/0031 |
| | | 604/119 |
| 2001/0016706 A1 | 8/2001 | Leukanech et al. |
| 2002/0062105 A1 | 5/2002 | Tanner |
| 2002/0077587 A1 * | 6/2002 | Boukhny et al. .......... 604/67 |
| 2003/0108429 A1 | 6/2003 | Angelini et al. |
| 2003/0199803 A1 | 10/2003 | Robinson et al. |
| 2004/0122381 A1 | 6/2004 | Arnold |
| 2004/0202561 A1 * | 10/2004 | Hershberger .... A61B 17/32002 |
| | | 417/477.7 |
| 2004/0253129 A1 * | 12/2004 | Sorensen et al. .......... 417/435 |
| 2005/0049539 A1 | 3/2005 | O'Hara, Jr. et al. |
| 2005/0095155 A1 | 5/2005 | Blight et al. |
| 2005/0100450 A1 | 5/2005 | Bryant et al. |
| 2005/0271531 A1 | 12/2005 | Brown, Jr. et al. |
| 2006/0000925 A1 | 1/2006 | Maher et al. |
| 2006/0093989 A1 | 5/2006 | Hahn et al. |

(56) References Cited

U.S. PATENT DOCUMENTS

| | | |
|---|---|---|
| 2006/0110274 A1 | 5/2006 | Gottschalk |
| 2006/0122556 A1 | 6/2006 | Kumar et al. |
| 2006/0245964 A1 | 11/2006 | Koslov |
| 2006/0253194 A1 | 11/2006 | Dial |
| 2007/0078370 A1 | 4/2007 | Shener et al. |
| 2007/0078379 A1* | 4/2007 | Boukhny et al. ............... 604/27 |
| 2007/0100316 A1 | 5/2007 | Traxinger |
| 2007/0135760 A1 | 6/2007 | Williams |
| 2007/0217919 A1 | 9/2007 | Gordan et al. |
| 2007/0278155 A1 | 12/2007 | Lo |
| 2007/0287959 A1 | 12/2007 | Walter et al. |
| 2008/0097320 A1 | 4/2008 | Moore et al. |
| 2008/0112828 A1 | 5/2008 | Muri et al. |
| 2008/0114289 A1 | 5/2008 | Muri et al. |
| 2008/0114291 A1 | 5/2008 | Muri et al. |
| 2008/0114301 A1 | 5/2008 | Bandhauer et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0200878 A1 | 8/2008 | Davis et al. |
| 2008/0220092 A1* | 9/2008 | Dipierro et al. ............. 424/649 |
| 2008/0240951 A1 | 10/2008 | Demash et al. |
| 2009/0012460 A1 | 1/2009 | Steck et al. |
| 2009/0018488 A1 | 1/2009 | Davis et al. |
| 2009/0035164 A1 | 2/2009 | Edwards |
| 2009/0060756 A1 | 3/2009 | Jones |
| 2009/0084718 A1 | 4/2009 | Prisco et al. |
| 2009/0246035 A1 | 10/2009 | Patzer |
| 2009/0299272 A1 | 12/2009 | Hopping et al. |
| 2009/0317271 A1 | 12/2009 | Gill et al. |
| 2010/0125257 A1 | 5/2010 | Perkins et al. |
| 2010/0130920 A1 | 5/2010 | Lo et al. |
| 2010/0130934 A1 | 5/2010 | Rochat |
| 2010/0145259 A1* | 6/2010 | Nash et al. ...................... 604/22 |
| 2010/0191178 A1* | 7/2010 | Ross et al. ...................... 604/22 |
| 2010/0228146 A1 | 9/2010 | Hibner |
| 2010/0241044 A1 | 9/2010 | Caleffi et al. |
| 2010/0280435 A1 | 11/2010 | Raney et al. |
| 2010/0286791 A1* | 11/2010 | Goldsmith .................. 623/23.7 |
| 2011/0092891 A1 | 4/2011 | Gerg et al. |
| 2011/0137231 A1* | 6/2011 | Sorensen et al. ............... 604/22 |
| 2011/0144567 A1* | 6/2011 | Sorensen et al. ............... 604/22 |
| 2012/0041358 A1 | 2/2012 | Mann et al. |
| 2012/0083728 A1* | 4/2012 | Sorensen et al. ............... 604/22 |

FOREIGN PATENT DOCUMENTS

| | | | |
|---|---|---|---|
| CA | 2743969 A1 | 3/2005 | |
| CA | 2649867 C | 6/2010 | |
| CN | 101023898 | 8/2007 | |
| CN | 200991440 Y | 12/2007 | |
| DE | 3809582 | 10/1989 | |
| DE | 19749358 | 5/1998 | |
| DE | 19711675 | 10/1998 | |
| DE | 19856744 | 6/2000 | |
| DE | 10034711 B4 | 2/2002 | |
| DE | 10034711 A1 | 4/2006 | |
| DE | 102007044790 | 4/2009 | |
| EP | 0200448 | 5/1986 | |
| EP | 200448 A2 | 5/1986 | |
| EP | 0200448 A2 * | 11/1986 | ............. F04B 43/12 |
| EP | 0320963 | 6/1989 | |
| EP | 0362822 A2 | 4/1990 | |
| EP | 518050 A1 | 12/1992 | |
| EP | 518050 B1 | 7/1996 | |
| EP | 0944404 A1 | 9/1999 | |
| EP | 1140257 A1 | 10/2001 | |
| EP | 1258260 A2 | 11/2002 | |
| EP | 964711 A1 | 4/2005 | |
| EP | 1810702 A1 | 7/2007 | |
| EP | 2173404 A1 | 4/2010 | |
| EP | 2509659 | 10/2012 | |
| FR | 2466641 | 4/1981 | |
| FR | 2797190 | 2/2001 | |
| GB | 2174763 | 11/1986 | |
| JP | 63-290564 | 11/1988 | |
| JP | 02070987 | 3/1990 | |
| JP | H03-164586 | 7/1991 | |
| JP | 2002-248117 | 9/2002 | |
| JP | 2003301778 A | 10/2003 | |
| JP | 2007-507636 | 3/2007 | |
| JP | 2007-198382 | 8/2007 | |
| JP | 2007-247646 | 9/2007 | |
| JP | 2008-546501 | 12/2008 | |
| RU | 2197277 | 1/2003 | |
| RU | 2241887 | 12/2004 | |
| SU | 1209928 A1 * | 2/1986 | |
| SU | 1533696 A1 | 1/1990 | |
| SU | 1590649 A1 * | 9/1990 | |
| WO | 98/18507 | 5/1998 | |
| WO | 98/24495 | 6/1998 | |
| WO | 99/38549 | 8/1999 | |
| WO | 2000/22995 | 4/2000 | |
| WO | 00/33898 | 6/2000 | |
| WO | 00/53136 | 9/2000 | |
| WO | WO 2003 073969 | 9/2003 | |
| WO | 2005009511 A2 | 2/2005 | |
| WO | 2005009511 A3 | 6/2005 | |
| WO | 2007001929 A2 | 1/2007 | |
| WO | 2008/131357 | 10/2008 | |
| WO | 09/005900 | 1/2009 | |
| WO | 09/146913 A2 | 12/2009 | |
| WO | 09/146913 A3 | 2/2010 | |
| WO | 10/061863 | 6/2010 | |
| WO | 10/129128 | 11/2010 | |
| WO | 2011/071775 | 6/2011 | |
| WO | 2011159428 A1 | 12/2011 | |
| WO | 2012048261 A2 | 4/2012 | |
| WO | 2012048261 A3 | 6/2012 | |

OTHER PUBLICATIONS

Written Opinion of the International Searching Authority, International Application No. PCT/US2010/058931, Feb. 1, 2011, 4 pages.
International Search Report for PCT/US2010/059032, filed Dec. 6, 2010, Publication No. 2011075332, Published Jun. 23, 2011, 2 pages.
Written Opinion of the International Searching Authority, International Application No. PCT/US2010/059032, Jan. 31, 2011, 5 pages.
(Citing Office Action) Examiner Edelmira Bosques, Non-Final Office Action, U.S. Appl. No. 12/637,886, Oct. 3, 2011, 11 pages.
Supplementary European Search Report for Application No. EP 10836456.3, Publication No. EP 2509659, Published Oct. 17, 2012, dated Mar. 20, 2013, 5 pages.
Supplementary European Search Report for Application No. EP 10838118.7, Publication No. EP2512554, Published Ot. 24, 2012, dated Apr. 15, 2013, 6 pages.
Milutinovic, et al., "Phacoemulsification Fluidics System Having a Single Pump Head," U.S. Appl. No. 12/818,682, filed Jun. 18, 2010, 28 pages.
International Searching Authority, Written Opinion of the International Searching Authority, International Application No. PCT/US2010/030168, Aug. 3, 2010, 8 pages.
International Search Report and Written Opinion of the International Searching Authority, International Application No. PCT/US2014/027271, filed Mar. 14, 2014, dated Jul. 28, 2014, 8 pages.
International Search Report and Written Opinion of the International Searching Authority, International Application No. PCT/US2014/027233, filed Mar. 14, 2014, dated Jul. 31, 2014, 10 pages.
International Search Report and Written Opinion of the International Searching Authority, International Application No. PCT/US2014/027307, filed Mar. 14, 2014, dated Jul. 30, 2014, 7 pages.
Sorensen, Gary, Phacoemulsification Hand Piece with Integrated Aspiration Pump, U.S. Appl. No. 13/325,549, filed Dec. 14, 2011, 18 pages.
http://www.advancedfluid.com/discflo/concepts.htm. Web archive dated Aug. 8, 2008, 3 pages.

(56) References Cited

OTHER PUBLICATIONS

Ovchinnikov et al., Acoustic Streaming of a Sharp Edge, Journal of Acoustical Society of America, 136 (1), Jul. 2014, pp. 22-29.

* cited by examiner

PHACOEMULSIFICATION HAND PIECE WITH INTEGRATED ASPIRATION PUMP

CROSS REFERENCE TO RELATED APPLICATIONS

This application is a continuation of prior application Ser. No. 12/633,363, filed Dec. 8, 2009.

BACKGROUND OF THE INVENTION

The present invention relates to phacoemulsification surgery and more particularly to a device that better regulates pressure experienced in the eye during cataract surgery.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece, an attached hollow cutting needle surrounded by an irrigating sleeve, and an electronic control console. The hand piece assembly is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece assembly.

The operative part in a typical hand piece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the hand piece by flexible mountings. The hand piece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigating sleeve.

During the phacoemulsification procedure, the tip of the cutting needle and the end of the irrigation sleeve are inserted into the anterior segment of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a waste reservoir.

Throughout the procedure, irrigating fluid is pumped into the eye, passing between the irrigation sleeve and the cutting needle and exiting into the eye at the tip of the irrigation sleeve and/or from one or more ports, or openings, cut into the irrigation sleeve near its end. This irrigating fluid is critical, as it prevents the collapse of the eye during the removal of the emulsified lens. The irrigating fluid also protects the eye tissues from the heat generated by the vibrating of the ultrasonic cutting needle. Furthermore, the irrigating fluid suspends the fragments of the emulsified lens for aspiration from the eye.

A common phenomenon during a phacoemulsification procedure arises from the varying flow rates that occur throughout the surgical procedure. Varying flow rates result in varying pressure losses in the irrigation fluid path from the irrigation fluid supply to the eye, thus causing changes in pressure in the anterior chamber (also referred to as Intra-Ocular Pressure or IOP.) Higher flow rates result in greater pressure losses and lower IOP. As IOP lowers, the operating space within the eye diminishes.

Another common complication during the phacoemulsification process arises from a blockage, or occlusion, of the aspirating needle. As the irrigation fluid and emulsified tissue is aspirated away from the interior of the eye through the hollow cutting needle, pieces of tissue that are larger than the diameter of the needle's bore may become clogged in the needle's tip. While the tip is clogged, vacuum pressure builds up within the tip. The resulting drop in pressure in the anterior chamber in the eye when the clog is removed is known as post-occlusion surge. This post-occlusion surge can, in some cases, cause a relatively large quantity of fluid and tissue to be aspirated out of the eye too quickly, potentially causing the eye to collapse and/or causing the lens capsule to be torn.

Various techniques, such as venting the aspiration line, have been designed to reduce this surge. However, there remains a need for improved phacoemulsification devices that reduce post-occlusion surge as well as maintain a stable IOP throughout varying flow conditions.

SUMMARY OF THE INVENTION

In one embodiment consistent with the principles of the present invention, the present invention is an ophthalmic surgical hand piece comprising a driver coupled to a horn, the horn coupled to a needle an aspiration pump integral with the hand piece, the aspiration pump located close to the needle; and a rigid length of aspiration line located between the aspiration pump and the needle.

In another embodiment consistent with the principles of the present invention, the present invention is an ophthalmic surgical hand piece comprising a driver coupled to a horn, the horn coupled to a needle an aspiration pump integral with the hand piece, the aspiration pump located close to the needle; a disposable segment coupled to the aspiration pump; and a rigid length of aspiration line located between the aspiration pump and the needle.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
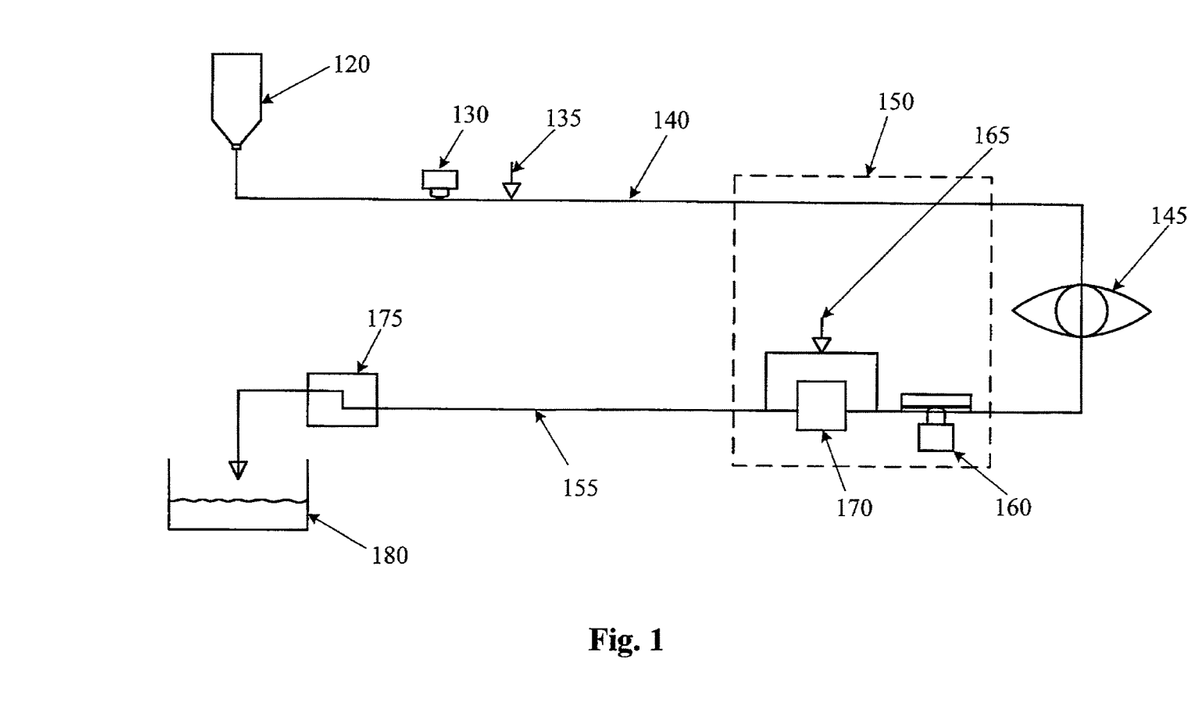
FIG. 1 is a diagram of the components in the fluid path of a phacoemulsification system including a hand piece with an integrated aspiration pump according to the principles of the present invention.

FIG. 1 is a diagram of the components in the fluid path of a phacoemulsification system including a hand piece with an integrated aspiration pump according to the principles of the present invention. FIG. 1 depicts the fluid path through the eye 145 during cataract surgery. The components include an irrigation source 120, an optional irrigation pressure sensor 130, an optional irrigation valve 135, an irrigation line 140, a hand piece 150, an aspiration line 155, an optional aspiration pressure sensor 160, an optional vent valve 165, a pump 170, a reservoir 175 and a drain bag 180. The irrigation line 140 provides irrigation fluid to the eye 145 during cataract surgery. The aspiration line 155 removes fluid and emulsified lens particles from the eye during cataract surgery.

When irrigation fluid exits irrigation source 120, it travels through irrigation line 140 and into the eye 145. An irrigation pressure sensor 130 measures the pressure of the irrigation fluid in irrigation line 140. An optional irrigation valve 135 is also provided for on/off control of irrigation. Irrigation pressure sensor 130 is implemented by any of a number of commercially available fluid pressure sensors.

A hand piece 150 is placed in relation to the eye 145 during a phacoemulsification procedure. The hand piece 150 has a hollow needle (270 in FIGS. 2 & 3) that is ultrasonically vibrated in the eye to break up the diseased lens. A sleeve located around the needle provides irrigation fluid from irrigation line 140. The irrigation fluid passes through the space between the outside of the needle and the inside of the sleeve. Fluid and lens particles are aspirated through the hollow needle. In this manner, the interior passage of the hollow needle is fluidly coupled to aspiration line 155. Pump 170 draws the aspirated fluid from the eye 145. An optional aspiration pressure sensor 160 measures the pressure in the aspiration line. An optional vent valve can be used to vent the vacuum created by pump 170. The aspirated fluid passes through reservoir 175 and into drain bag 180.

Figure 2:
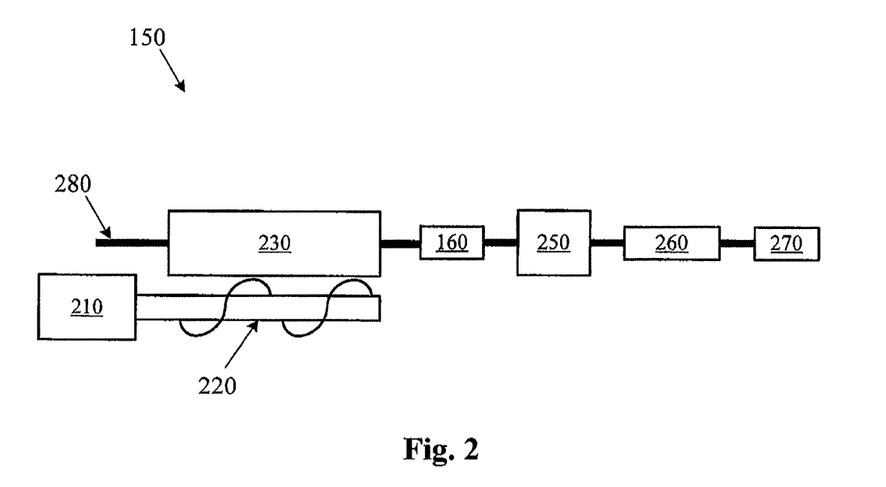
FIG. 2 is a block diagram of a phacoemulsification hand piece with an integrated aspiration pump according to the principles of the present invention.

FIG. 2 is a block diagram of a phacoemulsification hand piece with an integrated aspiration pump according to the principles of the present invention. In FIG. 2, hand piece 150 comprises motor 210, shaft 220, removable cartridge 230, optional aspiration pressure sensor 160, driver 250, horn 260, needle 270, and aspiration line 280. Motor 210 rotates shaft 220. When the pump is in operation, removable cartridge 230 is held against shaft 220. Aspiration pressure sensor 160 is located between removable cartridge 230 and the eye 145.

In FIG. 2, the pump 170 comprises motor 210, shaft 220, and flexible tubing in removable cartridge 230. In one embodiment of the present invention, shaft 220 has a spiral structure that presses against the flexible tubing in removable cartridge 230. In this manner, a screw-type or scroll-type aspiration pump is implemented with motor 210, shaft 220, and flexible tubing in removable cartridge 230. This is more clearly shown and described in FIGS. 4 and 5. While pump 170 is described as a screw-type pump, other types of pumps may also be used.

Aspiration line 280 is fluidly coupled to removable cartridge 230. Aspiration line also extends through or around drive 250, horn 260, and needle 270. A lumen in needle 270 is fluidly coupled to aspiration line 280. As described above, fluid and lens particles are aspirated through the lumen of needle 270. Aspiration pump 170 draws fluid and lens particles through the lumen of needle 270.

Driver 250 is typically an ultrasonic driver that produces ultrasonic vibrations in horn 260. Horn 260 is typically a mass of metal that is coupled to driver 250 and needle 270. In this manner, vibrations produced by driver 250 are transferred to horn 260 and to needle 270. Needle 270 is placed in the eye and vibrated to fragment a cataractous lens.

Aspiration pressure sensor 160 measures the aspiration pressure in aspiration line 280. While shown as located between removable cartridge 230 and driver 250, aspiration pressure sensor may be located at any location between pump 170 and the eye 145. Aspiration pressure sensor 160 may be implemented by any of a number of known pressure sensor devices.

Figure 3:
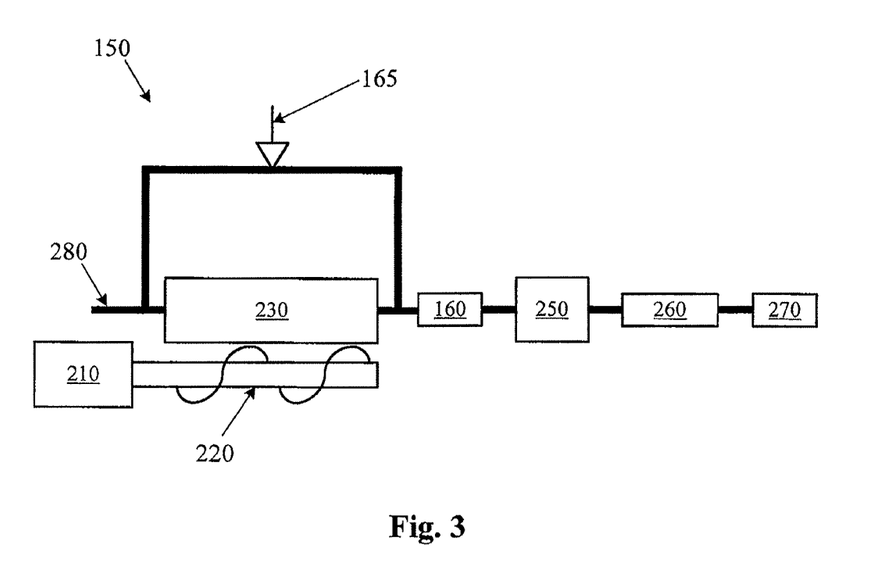
FIG. 3 is a block diagram of a phacoemulsification hand piece with an integrated aspiration pump according to the principles of the present invention.

FIG. 3 is a block diagram of a phacoemulsification hand piece with an integrated aspiration pump according to the principles of the present invention. The example of FIG. 3 has the elements of FIG. 2 plus an optional vent valve 165. When optional vent valve 165 is present, it acts to provide a venting path for the aspiration pump 170. In this manner, pump 170 can be vented, for example, to atmosphere when vent valve 165 is opened. As shown in FIG. 3, aspiration line 280 has two paths—one path that goes through removable cartridge 230, and another path that goes around removable cartridge 230. This second path (that goes around removable cartridge 230) and associated vent valve 165 may also be incorporated into removable cartridge 230. When vent valve 165 is opened, the aspiration or vacuum produced by pump 170 is decreased as a result of it being vented to atmosphere.

Figure 4:
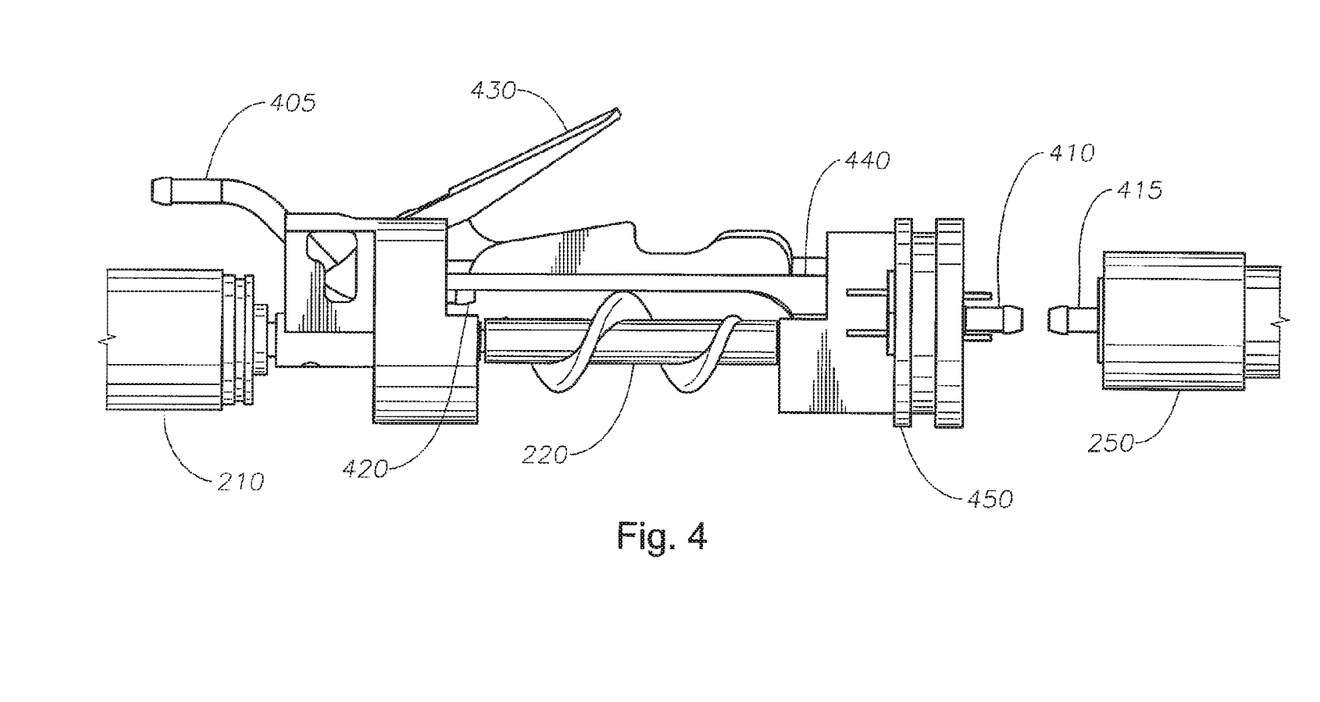
FIG. 4 is a side view of a portion of a phacoemulsification hand piece with an integrated aspiration pump according to the principles of the present invention.
Figure 5:
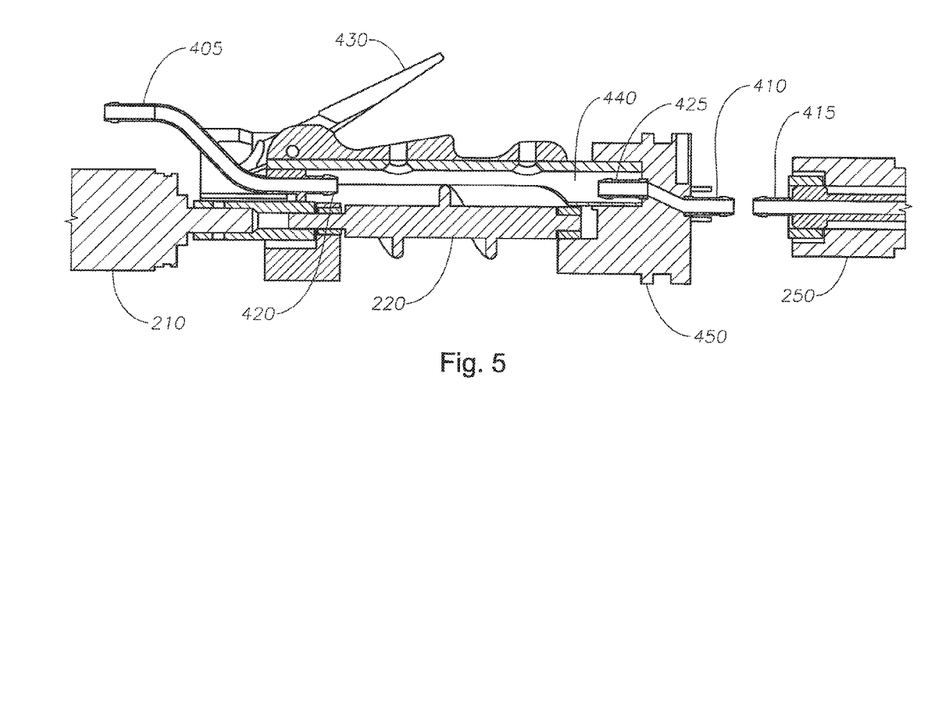
FIG. 5 is a cross section view of a portion of a phacoemulsification hand piece with an integrated aspiration pump according to the principles of the present invention.

FIGS. 4 and 5 are side and cross section views, respectively, of a portion of a phacoemulsification hand piece with an integrated aspiration pump according to the principles of the present invention. FIGS. 4 and 5 more clearly show the details of one example of a removable cartridge 230 and pump 170. In the example shown, removable cartridge 230 comprises aspiration line coupling 405, first tubing coupling 420, tubing holder 440, and lever 430. These components are integrated into a frame as shown. Removable cartridge 230 can be removed from the remainder of the hand piece.

In the example of the removable cartridge shown in FIGS. 4 and 5, aspiration line coupling 405 can be attached to aspiration tubing that is coupled to the surgical console. In this manner, aspiration line coupling 405 is near the end of the hand piece that is connected to the surgical console. A tube extends from aspiration line coupling 405 to first tubing coupling 420. This tube is a part of the aspiration line 280 shown in FIGS. 2 and 3.

Tubing holder 440 holds a flexible tube (not shown) that is located between shaft 220 and tubing holder 440. Shaft 220 presses the flexible tubing against tubing holder 440. As shaft 220 rotates, the spiral protrusion on shaft 220 pumps fluid through the flexible tubing (thus implementing a screw-type or scroll-type pump). Tubing holder 440 is made of a rigid material that is suitable for holding flexible tubing. One end of the flexible tubing is fluidly coupled to first tubing coupling 420, and the other end of the flexible tubing is fluidly coupled to second tubing coupling 425. In this manner, the flexible tubing is a part of the aspiration line 280.

Lever 430 operates to secure removable cartridge 230 to the remainder of the hand piece. While shown as a lever, other mechanisms can be employed to secure removable cartridge to the remainder of the hand piece.

Motor 210 is coupled to shaft 220 and serves to rotate shaft 220. Motor 210 can be controlled to control the movement of shaft 220 as more clearly described below. Motor 210 is typically a DC motor but can be any type of motor or driver suitable for rotating shaft 220.

In the example of FIGS. 4 and 5, a connector 450 connects the flexible tubing held by tubing holder 440 to the hand piece coupling 415. Connector coupling 410 interfaces with hand piece coupling 415—either directly or via another part. In this manner, the aspiration path passes through hand piece coupling 415, connector coupling 410, connector 450, second tubing coupling 425, the flexible tubing held by tubing holder 440, first tubing coupling 420 and aspiration line coupling 405. Connector 450 is connected to an end of shaft 220. In this manner, connector 450, shaft 220, and motor 210 (along with the frame that holds these parts) is attached to the driver 250 (which is coupled to the horn 260 and the needle 270).

The length of aspiration line between the pump and the eye (i.e. between second tubing coupling 425 and needle 270) is minimal (on the order of inches). In addition, this length of aspiration line between the pump and the eye may be non-compliant (i.e. it can be rigid). Having a small length of non-compliant tubing between the pump 170 and the eye eliminates the surge associated with prior art systems.

In operation, motor 210 rotates shaft 220. A controller (not shown) controls the operation of motor 210. In this manner, shaft 220 may be rotated at any desired speed to produce any desired vacuum. Further, shaft 220 may be stopped or rotated in an opposite direction if desired. In this manner, motor 210 may be controlled to rotate shaft 220 in either direction. When rotated, shaft 220 draws fluid through the flexible tube and acts to pump the fluid through the aspiration line.

In another example, shaft 220 can be moved toward and away from tubing holder 440. In this manner, the space between tubing holder 440 and shaft 220 can be varied so that the flexible tubing can be pinched to different degrees between shaft 220 and tubing holder 440. In other words, shaft 220 can pinch the flexible tubing held by tubing holder 440 very tightly to produce pumping action that does not allow for leakage. Alternatively, as shaft 220 is moved away from tubing holder 440, the flexible tubing is pinched less tightly thus leading to a leakage and less of a vacuum or pumping force. The position of shaft 220 with respect to tubing holder 440 can be variably controlled to adjust the leakage through the flexible tubing, and in turn adjust the vacuum produced by the pump.

In another example (shown in FIG. 3), the position of shaft 220 with respect to tubing holder 440 can be fixed, and a vent valve 165 can be used to produce leakage that adjusts the vacuum produced by the pump. In this manner, vent valve 165 can be variably controlled to control the amount of vacuum that is present in the aspiration line (by controlling the amount of leakage through vent valve 165).

The control of aspiration vacuum can be based on a reading from aspiration pressure sensor 160. Aspiration pressure sensor 160 is located between the pump and the eye. In this manner, aspiration pressure sensor 160 accurately reads the pressure conditions in the aspiration line very close to the eye. Such a reading can be used to precisely control the aspiration vacuum that is applied to the eye.

Figure 6:
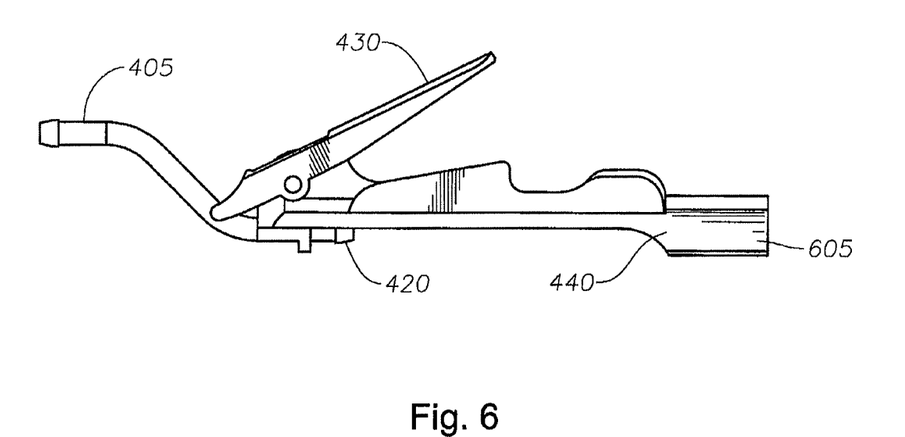
FIG. 6 is a side view of a removable cartridge for use with a phacoemulsification hand piece with an integrated aspiration pump according to the principles of the present invention.
Figure 7:
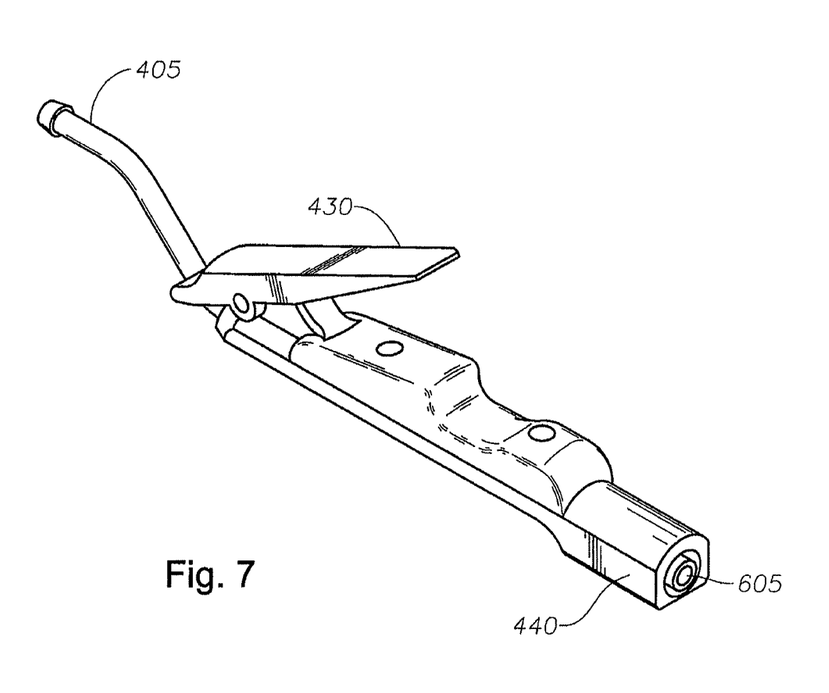
FIG. 7 is a perspective view of a removable cartridge for use with a phacoemulsification hand piece with an integrated aspiration pump according to the principles of the present invention.

FIGS. 6 and 7 are side and perspective views, respectively, of a removable cartridge for use with a phacoemulsification hand piece with an integrated aspiration pump according to the principles of the present invention. In the example of FIGS. 6 and 7, the removable cartridge comprises aspiration line coupling, 405, first tubing coupling 420, tubing holder 440, lever 430, and opening 605. Opening 605 interfaces with second tubing coupling 425 as shown in FIG. 5. A piece of flexible tubing is located between first tubing coupling 420 and opening 605. The removable cartridge 230 of FIGS. 6 and 7 can be reusable or disposable. In one example, the removable cartridge is reusable and the flexible tubing in disposable. In another example, the removable cartridge is disposable along with the flexible tubing.

The design of the present invention allows for the aspiration pump 170 to be very close to the eye 145. The distance between the aspiration pump 170 and the eye 145 can be made to be very small—on the order of inches. Placing the aspiration pump 170 close to the eye 145 allows for a very short length of aspiration line to be located between the pump 170 and the eye 145. Moreover, the length of aspiration line located between the pump 170 and the eye 145 can be rigid (for example, it can be made of stainless steel). This short length of non-compliant material that makes up the aspiration line between the pump 170 and the eye 145 eliminates any surge effect associated with conventional phacoemulsification systems.

In conventional phacoemulsification systems, the aspiration pump is located in a console. A relatively long length of flexible tubing (six feet or more) is located between the aspiration pump and the eye. This relatively long length of flexible tubing has a lot of compliance—it can stretch in response to changes in vacuum pressure. This compliance results in surges as previously described. By incorporating the aspiration pump in the hand piece (and placing it very close to the eye) and having a very short length of non-compliant tubing between the aspiration pump and the eye, these surges can be eliminated, thus resulting in a safer and more efficient surgery.

From the above, it may be appreciated that the present invention provides a pressurized infusion system for phacoemulsification surgery. The present invention provides an irrigation squeeze band device that more precisely controls fluid pressure. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ophthalmic surgical hand piece comprising:
   a driver coupled to a horn, the horn coupled to a needle;
   an aspiration pump integral with the hand piece, the aspiration pump located close to the needle, the aspiration pump comprising:
      a motor; and
      a shaft having a spiral structure coupled to the motor;
   a rigid length of aspiration line located between the aspiration pump and the needle, and
   a removable cartridge, the removable cartridge comprising:
      a flexible tubing pressed against the spiral structure operable to cause movement of fluid within the flexible tubing as the shaft is rotated by the motor; and
      a securing mechanism operable to secure the removable cartridge to a remainder of the hand piece.

2. The hand piece of claim 1 further comprising:
   an aspiration pressure sensor located between the removable cartridge and the needle.

3. The hand piece of claim 1 further comprising:
   a vent valve located in parallel with the aspiration pump, the vent valve being variably controlled to variably control a vacuum produced by the aspiration pump.

4. The hand piece of claim 1 further comprising:
   a moveable member that engages a flexible length of aspiration line, a position of the moveable member with respect to the flexible length of aspiration line determining a leakage that decreases vacuum pressure in the rigid length of aspiration line.

5. An ophthalmic surgical hand piece comprising:
   a driver coupled to a horn, the horn coupled to a needle;
   an aspiration pump integral with the hand piece, the aspiration pump located close to the needle, the aspiration pump comprising:
      a motor; and
      a shaft having a spiral structure coupled to the motor;
   a disposable segment coupled to the aspiration pump, the disposable segment comprising:
      a flexible tubing pressed against the spiral structure operable to cause movement of fluid within the flexible tubing as the shaft is rotated by the motor; and
      a securing mechanism operable to secure the disposable segment; and
   a rigid length of aspiration line located between the aspiration pump and the needle.

6. The hand piece of claim 5 further comprising:
   an aspiration pressure sensor located between the disposable segment and the needle.

7. The hand piece of claim 5 further comprising:
   a vent valve located in parallel with the aspiration pump, the vent valve being variably controlled to variably control a vacuum produced by the aspiration pump.

8. The hand piece of claim 5 further comprising:
   a moveable member that engages disposable segment, a position of the moveable member with respect to the disposable segment determining a leakage that decreases vacuum pressure in the rigid length of aspiration line.

* * * * *

UNITED STATES PATENT AND TRADEMARK OFFICE
CERTIFICATE OF CORRECTION

PATENT NO. : 9,861,522 B2
APPLICATION NO. : 13/325549
DATED : January 9, 2018
INVENTOR(S) : Sorensen et al.

Page 1 of 1

It is certified that error appears in the above-identified patent and that said Letters Patent is hereby corrected as shown below:

On the Title Page

Item (75) Inventor is corrected to read:
-- Gary Sorensen, Laguna Niguel, (CA);
Glenn Sussman, Laguna Niguel, (CA);
Larry L. Hood, Irvine, (CA) --.

Signed and Sealed this
Thirteenth Day of August, 2019

Andrei Iancu
*Director of the United States Patent and Trademark Office*